US009978278B2

(12) United States Patent
Boesen

(10) Patent No.: US 9,978,278 B2
(45) Date of Patent: May 22, 2018

(54) VEHICLE TO VEHICLE COMMUNICATIONS USING EAR PIECES

(71) Applicant: BRAGI GmbH, München (DE)

(72) Inventor: Peter Vincent Boesen, München (DE)

(*) Notice: Subject to any disclaimer, the term of this patent is extended or adjusted under 35 U.S.C. 154(b) by 0 days. days.

(21) Appl. No.: 15/357,127

(22) Filed: Nov. 21, 2016

(65) Prior Publication Data

US 2017/0154532 A1 Jun. 1, 2017

Related U.S. Application Data

(60) Provisional application No. 62/260,447, filed on Nov. 27, 2015.

(51) Int. Cl.
| | | |
|---|---|---|
| *G08G 1/16* | (2006.01) | |
| *H04B 1/3827* | (2015.01) | |
| *H04W 84/18* | (2009.01) | |

(52) U.S. Cl.
CPC ............ *G08G 1/161* (2013.01); *H04B 1/385* (2013.01); *H04W 84/18* (2013.01); *H04B 2001/3866* (2013.01)

(58) Field of Classification Search
CPC ... A61B 5/117; A61B 5/02055; B60R 16/037; B60R 25/257; B60W 40/08; B60W 50/12; G01C 21/3423; G05D 1/0016; G07C 5/008; G08G 1/161; H04B 1/385; H04B 2001/3866; H04M 1/0256; H04M 1/6066; H04R 1/1016; H04R 1/1041; H04R 1/1083; H04R 1/1091; H04R 2201/107;

(Continued)

(56) References Cited

U.S. PATENT DOCUMENTS

| | | |
|---|---|---|
| 3,934,100 A | 1/1976 | Harada |
| 4,150,262 A | 4/1979 | Ono |

(Continued)

FOREIGN PATENT DOCUMENTS

| | | |
|---|---|---|
| CN | 204244472 U | 4/2015 |
| CN | 104837094 A | 8/2015 |

(Continued)

OTHER PUBLICATIONS

Announcing the $3,333,333 Stretch Goal (Feb. 24, 2014).

(Continued)

*Primary Examiner* — Quan-Zhen Wang
*Assistant Examiner* — Stephen Burgdorf
(74) *Attorney, Agent, or Firm* — Goodhue, Coleman & Owens, P.C.

(57) ABSTRACT

A system includes a vehicle, a vehicle network disposed within the vehicle, and at least one earpiece for use within the vehicle. The vehicle is configured to wirelessly communicate with the at least one wireless earpiece within the vehicle. The vehicle is configured to wirelessly communication with at least one wireless earpiece within a separate and independent vehicle. A method includes sensing data with a sensor of a wireless earpiece within a first vehicle to provide sensed data, determining by the wireless earpiece within the first vehicle an alert condition based on the sensed data, and wirelessly communicating a message from a wireless earpiece within a first vehicle to a wireless ear piece within a second vehicle, the message indicating occurrence of the alert condition.

9 Claims, 6 Drawing Sheets

(58) Field of Classification Search
CPC ........... H04R 2420/07; H04R 2460/13; H04W 4/046; H04W 84/18
USPC .......................................... 340/902; 381/328
See application file for complete search history.

(56) References Cited

U.S. PATENT DOCUMENTS

| | | | |
|---|---|---|---|
| 4,334,315 A | 6/1982 | Ono et al. | |
| 4,375,016 A | 2/1983 | Harada | |
| 4,588,867 A | 5/1986 | Konomi | |
| 4,654,883 A | 3/1987 | Iwata | |
| 4,682,180 A | 7/1987 | Gans | |
| 4,791,673 A | 12/1988 | Schreiber | |
| 4,865,044 A | 9/1989 | Wallace et al. | |
| 5,191,602 A | 3/1993 | Regen et al. | |
| 5,201,007 A | 4/1993 | Ward et al. | |
| 5,280,524 A | 1/1994 | Norris | |
| 5,295,193 A | 3/1994 | Ono | |
| 5,298,692 A | 3/1994 | Ikeda et al. | |
| 5,343,532 A | 8/1994 | Shugart | |
| 5,363,444 A | 11/1994 | Norris | |
| 5,497,339 A | 3/1996 | Bernard | |
| 5,606,621 A | 2/1997 | Reiter et al. | |
| 5,613,222 A | 3/1997 | Guenther | |
| 5,692,059 A | 11/1997 | Kruger | |
| 5,721,783 A | 2/1998 | Anderson | |
| 5,749,072 A | 5/1998 | Mazurkiewicz et al. | |
| 5,771,438 A | 6/1998 | Palermo et al. | |
| 5,802,167 A | 9/1998 | Hong | |
| 5,929,774 A | 7/1999 | Charlton | |
| 5,933,506 A | 8/1999 | Aoki et al. | |
| 5,949,896 A | 9/1999 | Nageno et al. | |
| 5,987,146 A | 11/1999 | Pluvinage et al. | |
| 6,021,207 A | 2/2000 | Puthuff et al. | |
| 6,041,410 A | 3/2000 | Hsu et al. | |
| 6,054,989 A | 4/2000 | Robertson et al. | |
| 6,081,724 A | 6/2000 | Wilson | |
| 6,094,492 A | 7/2000 | Boesen | |
| 6,111,569 A | 8/2000 | Brusky et al. | |
| 6,112,103 A | 8/2000 | Puthuff | |
| 6,140,939 A | 10/2000 | Flick | |
| 6,157,727 A | 12/2000 | Rueda | |
| 6,167,039 A | 12/2000 | Karlsson et al. | |
| 6,181,801 B1 | 1/2001 | Puthuff et al. | |
| 6,208,372 B1 | 3/2001 | Barraclough | |
| 6,275,789 B1 | 8/2001 | Moser et al. | |
| 6,339,754 B1 | 1/2002 | Flanagan et al. | |
| 6,408,081 B1 | 6/2002 | Boesen | |
| D464,039 S | 10/2002 | Boesen | |
| 6,470,893 B1 | 10/2002 | Boesen | |
| D468,299 S | 1/2003 | Boesen | |
| D468,300 S | 1/2003 | Boesen | |
| 6,542,721 B2 | 4/2003 | Boesen | |
| 6,560,468 B1 | 5/2003 | Boesen | |
| 6,654,721 B2 | 11/2003 | Handelman | |
| 6,664,713 B2 | 12/2003 | Boesen | |
| 6,694,180 B1 | 2/2004 | Boesen | |
| 6,718,043 B1 | 4/2004 | Boesen | |
| 6,738,485 B1 | 5/2004 | Boesen | |
| 6,748,095 B1 | 6/2004 | Goss | |
| 6,754,358 B1 | 6/2004 | Boesen et al. | |
| 6,784,873 B1 | 8/2004 | Boesen et al. | |
| 6,823,195 B1 | 11/2004 | Boesen | |
| 6,852,084 B1 | 2/2005 | Boesen | |
| 6,879,698 B2 | 4/2005 | Boesen | |
| 6,892,082 B2 | 5/2005 | Boesen | |
| 6,920,229 B2 | 7/2005 | Boesen | |
| 6,952,483 B2 | 10/2005 | Boesen et al. | |
| 6,987,986 B2 | 1/2006 | Boesen | |
| 7,136,282 B1 | 11/2006 | Rebeske | |
| 7,203,331 B2 | 4/2007 | Boesen | |
| 7,209,569 B2 | 4/2007 | Boesen | |
| 7,215,790 B2 | 5/2007 | Boesen et al. | |
| 7,463,902 B2 | 12/2008 | Boesen | |
| 7,508,411 B2 | 3/2009 | Boesen | |
| 7,983,628 B2 | 7/2011 | Boesen | |
| 8,108,143 B1 | 1/2012 | Tester | |
| 8,140,357 B1 | 3/2012 | Boesen | |
| 8,610,585 B1* | 12/2013 | Kielbasa | G08B 21/06 180/271 |
| 8,994,498 B2 | 3/2015 | Agrafioti et al. | |
| 9,037,125 B1 | 5/2015 | Kadous | |
| 9,081,944 B2 | 7/2015 | Camacho et al. | |
| 9,272,711 B1* | 3/2016 | Sivaraman | G08G 1/166 |
| 9,510,159 B1 | 11/2016 | Cuddihy et al. | |
| 2001/0005197 A1 | 6/2001 | Mishra et al. | |
| 2001/0027121 A1 | 10/2001 | Boesen | |
| 2001/0056350 A1 | 12/2001 | Calderone et al. | |
| 2002/0002413 A1 | 1/2002 | Tokue | |
| 2002/0007510 A1 | 1/2002 | Mann | |
| 2002/0010590 A1 | 1/2002 | Lee | |
| 2002/0030637 A1 | 3/2002 | Mann | |
| 2002/0046035 A1 | 4/2002 | Kitahara et al. | |
| 2002/0057810 A1 | 5/2002 | Boesen | |
| 2002/0076073 A1 | 6/2002 | Taenzer et al. | |
| 2002/0118852 A1 | 8/2002 | Boesen | |
| 2003/0002705 A1 | 1/2003 | Boesen | |
| 2003/0065504 A1 | 4/2003 | Kraemer et al. | |
| 2003/0100331 A1 | 5/2003 | Dress et al. | |
| 2003/0104806 A1 | 6/2003 | Ruef et al. | |
| 2003/0115068 A1 | 6/2003 | Boesen | |
| 2003/0125096 A1 | 7/2003 | Boesen | |
| 2003/0218064 A1 | 11/2003 | Conner et al. | |
| 2004/0070564 A1 | 4/2004 | Dawson et al. | |
| 2004/0124968 A1 | 7/2004 | Inada et al. | |
| 2004/0160511 A1 | 8/2004 | Boesen | |
| 2005/0017842 A1 | 1/2005 | Dematteo | |
| 2005/0043056 A1 | 2/2005 | Boesen | |
| 2005/0125320 A1 | 6/2005 | Boesen | |
| 2005/0148883 A1 | 7/2005 | Boesen | |
| 2005/0165663 A1 | 7/2005 | Razumov | |
| 2005/0196009 A1 | 9/2005 | Boesen | |
| 2005/0251455 A1 | 11/2005 | Boesen | |
| 2005/0266876 A1 | 12/2005 | Boesen | |
| 2006/0029246 A1 | 2/2006 | Boesen | |
| 2006/0074671 A1 | 4/2006 | Farmaner et al. | |
| 2006/0074808 A1 | 4/2006 | Boesen | |
| 2006/0220915 A1 | 10/2006 | Bauer | |
| 2008/0146890 A1* | 6/2008 | LeBoeuf | A61B 5/0059 600/300 |
| 2008/0254780 A1 | 10/2008 | Kuhl et al. | |
| 2009/0003620 A1 | 1/2009 | McKillop et al. | |
| 2009/0128286 A1 | 5/2009 | Vitito | |
| 2009/0191920 A1 | 7/2009 | Regen et al. | |
| 2009/0238386 A1 | 9/2009 | Usher et al. | |
| 2010/0033313 A1 | 2/2010 | Keady et al. | |
| 2010/0210212 A1 | 8/2010 | Sato | |
| 2011/0215921 A1 | 9/2011 | Ayed et al. | |
| 2013/0090744 A1* | 4/2013 | Tran | G05B 11/01 700/9 |
| 2013/0329051 A1 | 12/2013 | Boesen | |
| 2014/0163771 A1 | 6/2014 | Demeniuk | |
| 2014/0185828 A1 | 7/2014 | Helbling | |
| 2014/0270227 A1 | 9/2014 | Swanson | |
| 2015/0028996 A1 | 1/2015 | Agrafioti et al. | |
| 2015/0148989 A1 | 5/2015 | Cooper et al. | |
| 2015/0243172 A1* | 8/2015 | Eskilson | H04L 67/12 701/1 |
| 2015/0379859 A1* | 12/2015 | Nespolo | G08B 21/24 340/539.32 |
| 2016/0001781 A1* | 1/2016 | Fung | G06F 19/345 701/36 |
| 2016/0033280 A1 | 2/2016 | Moore et al. | |
| 2016/0227009 A1 | 8/2016 | Kim et al. | |
| 2017/0153636 A1 | 6/2017 | Boesen | |

FOREIGN PATENT DOCUMENTS

| | | |
|---|---|---|
| EP | 1017252 A2 | 7/2000 |
| EP | 1469659 A1 | 10/2004 |
| GB | 2074817 | 4/1981 |
| JP | 06292195 | 10/1998 |
| NO | 2014046602 A1 | 3/2014 |

(56) References Cited

FOREIGN PATENT DOCUMENTS

| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People ©BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, on Track and Gems Overview (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Last Push Before the Kickstarter Campaign Ends on Monday 4pm CET (Mar. 28, 2014).
Nigel Whitfield: "Fake tape detectors, 'from the stands' footle and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash +The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
International Search & Written Opinion, PCT/EP16/78788 (dated Mar. 20, 2017).
Akkermans, "Acoustic Ear Recognition for Person Identification", Automatic Identification Advanced Technologies, 2005 pp. 219-223.
BMW, "BMW introduces BMW Connected—The personalized digital assistant", "http://bmwblog.com/2016/01/05/bmw-introduces-bmw-connected-the-personalized-digital-assistant", (Jan. 5, 2016).
Hyundai Motor America, "Hyundai Motor Company Introduces a Health + Mobility Concept for Wellness in Mobility",Fountain Valley, Californa (2017).

\* cited by examiner

VEHICLE TO VEHICLE COMMUNICATIONS USING EAR PIECES

PRIORITY STATEMENT

This application claims priority to U.S. Provisional Patent Application 62/260,447, filed on Nov. 27, 2015, and entitled Vehicle to vehicle communications using ear pieces, hereby incorporated by reference in its entirety.

FIELD OF THE INVENTION

The present invention relates to wearable devices. More particularly, but not exclusively, the present invention relates to ear pieces used within vehicles for vehicle to vehicle communications.

BACKGROUND

Vehicles may come with various types of electronics packages. These packages may be standard or optional and include electronics associated with communications, navigation, or entertainment. However, there are various problems and deficiencies with such offerings. What is needed are vehicles with improved electronics options which create, improve, or enhance safety or overall experience of vehicles. In particular, what is needed are vehicles which integrate with wearable devices.

SUMMARY

Therefore, it is a primary object, feature, or advantage of the present invention to improve over the state of the art.

It is another object, feature, or advantage of the present invention to communicate between vehicle systems and wearable devices.

It is a further object, feature, or advantage of the present invention to use wearable devices within vehicles and to provide enhanced vehicle functionality.

It is another object, feature, or advantage of the present invention to collect information from a vehicle and to communicate to a wearable device such as an earpiece.

According to one aspect a system includes a vehicle, a vehicle network disposed within the vehicle, and at least one earpiece for use within the vehicle. The vehicle is configured to wirelessly communicate with and receive sensor data from the at least one wireless earpiece within the vehicle. The vehicle is configured to receive sensor data from at least one wireless earpiece within a separate and independent vehicle. The vehicle may be configured to receive sensor data from the at least one wireless earpiece within the vehicle and/or the at least one wireless earpiece within the separate and independent vehicle and perform a vehicle operation based on the sensor data from the at least one wireless earpiece within the vehicle and/or the at least one wireless earpiece within the separate and independent vehicle. The sensor data from the at least one wireless earpiece within the separate and independent vehicle may be communicated between the vehicle network of the vehicle and a vehicle network of the separate and independent vehicle. The sensor data from the at least one wireless earpiece within the separate and independent vehicle may be communicated to the at least one wireless earpiece within the vehicle and from the at least one wireless earpiece within the vehicle to the vehicle network of the vehicle. The at least one earpiece for use within the vehicle may include an inertial sensor and may be used to determine a warning condition based on sensed data from the inertial sensor. The vehicle network may be configured to electronically send a warning message to the wireless earpiece within the separate and independent vehicle. The vehicle network may be configured to electronically receive a warning message from the wireless earpiece within the separate and independent vehicle. The at least one earpiece may include a health monitoring sensor and may be configured to determine a warning condition based on sensed data from the health monitoring data.

According to another aspect a method includes sensing data with a sensor of a wireless earpiece within a first vehicle to provide sensed data, determining by the wireless earpiece within the first vehicle an alert condition based on the sensed data, and wirelessly communicating a message from a wireless earpiece within the first vehicle to a wireless ear piece within a second vehicle, the message indicating occurrence of the alert condition. The sensor may be an inertial sensor and the sensed data may include inertial data. The sensor may be a physiological sensor and the sensed data may be physiological data.

According to another aspect, a method includes sensing data with a sensor of a wireless earpiece within a first vehicle to provide sensed data, determining by the wireless earpiece within the first vehicle an alert condition based on the sensed data, and wirelessly communicating a message from a wireless earpiece within a first vehicle to a second vehicle, the message indicating occurrence of the alert condition. The sensor may be an inertial sensor and the sensed data may be inertial data. The sensor may be a physiological sensor and the sensed data may be physiological data.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

DETAILED DESCRIPTION

Some of the most important factors in selecting a vehicle such as a car may be the technology available to enhance the experience. This may be of particular importance in certain vehicle segments such as for luxury vehicles. Another important factor in selecting a vehicle may be the available safety features. According to various aspects, the present invention allows for wearable devices including ear pieces to enhance the experience of vehicles and according to some aspects, the present invention allows for wearable devices such as earpieces to enhance the overall safety of the vehicle. Therefore, it is expected that the technology described herein will make any vehicle so equipped more desirable to customers, more satisfying to customers, and potentially more profitable for the vehicle manufacturer. Similarly at least some of the various aspects may be added to existing vehicles as after-market accessories to improve the safety or experience of existing vehicles.

Figure 1:
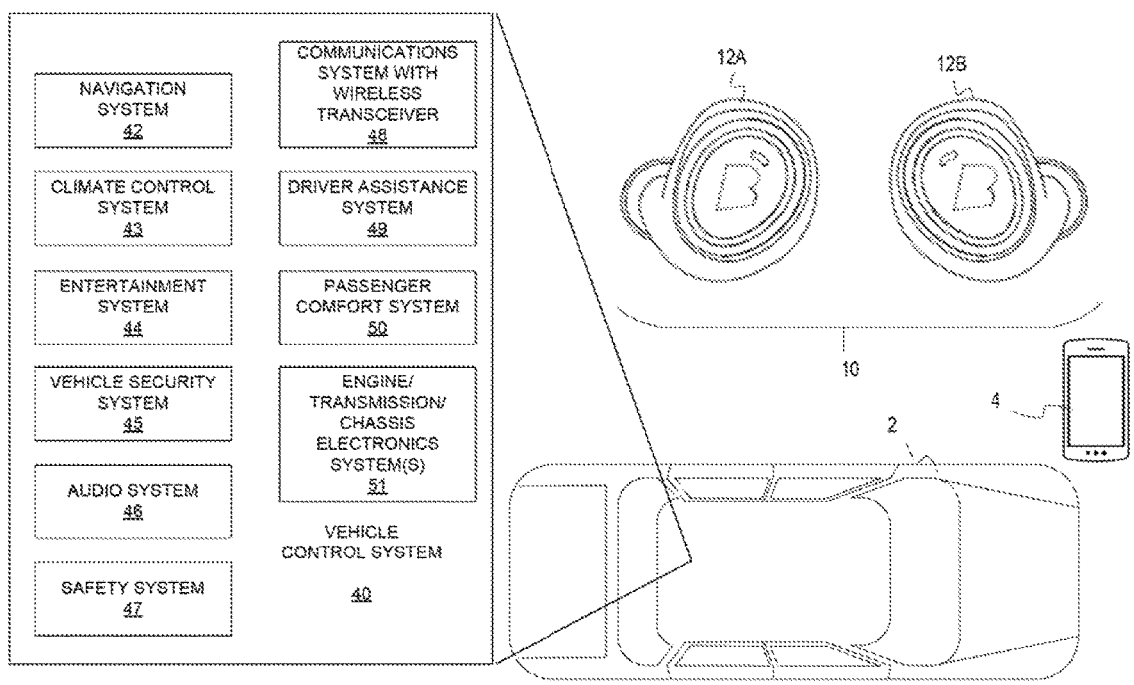
FIG. 1 illustrates one example of use of a wearable device in conjunction with a vehicle.

FIG. 1 illustrates one example of use of a wearable device in conjunction with a vehicle. As shown in FIG. 1 there is a vehicle 2. Although the vehicle shown is a full-size sedan, it is contemplated that the vehicle may be of any number of types of cars, trucks, sport utility vehicles, vans, mini-vans, automotive vehicles, commercial vehicles, agricultural vehicles, construction vehicles, specialty vehicles, recreational vehicles, buses, motorcycles, aircraft, boats, ships, yachts, spacecraft, or other types of vehicles. The vehicle may be gas-powered, diesel powered, electric, solar-powered, or human-powered. The vehicle may be actively operated by a driver or may be partially or completely autonomous or self-driving. The vehicle 2 may have a vehicle control system 40. The vehicle control system 40 is a system which may include any number of mechanical, electrical, and electromechanical subsystems. As shown in FIG. 1, such systems may include a navigation system 42, a climate control system 43, an entertainment system 44, a vehicle security system 45, an audio system 46, a safety system 47, a communications system 48 preferably with a wireless transceiver, a driver assistance system 49, a passenger comfort system 50, and an engine/transmission, chassis electronics system(s) 51. Of course, other examples of vehicle control sub-systems are contemplated. In addition, it is to be understood that there may be overlap between some of these different vehicle systems and the presence or absence of these vehicle systems as well as other vehicle systems may depend upon the type of vehicle, the type of fuel or propulsion system, the size of the vehicle, and other factors and variables. In the automotive context, examples of the driver assistance system 49 may include one or more subsystems such as a lane assist system, a speed assist system, a blind spot detection system, a park assist system, and an adaptive cruise control system. In the automotive context, examples of the passenger comfort system 50 may include one or more subsystems such as automatic climate control, electronic seat adjustment, automatic wipers, automatic headlamps, and automatic cooling. In the automotive context, examples of the safety system 47 may include active safety systems such as air bags, hill descent control, and an emergency brake assist system. Aspects of the navigation system 42, the entertainment system 44, the audio system 46, and the communications system 48 may be combined into an infotainment system.

One or more wearable devices such as a set of earpieces 10 including a left earpiece 12A and a right earpiece 12B may be in operative communication with the vehicle control system 40 such as through the communication system 48. For example, the communication system 48 may provide a Bluetooth or BLE link or Wi-Fi link to wearable devices or may otherwise provide for radio communications or other types of communications with the wearable devices. Preferably the communications are wireless communications. The vehicle 2 may communicate with the wearable device(s) directly, or alternatively, or in addition, the vehicle 2 may communicate with the wearable device(s) through an intermediary device such as a mobile device 4 which may be a mobile phone, a tablet, or other type of mobile device or computing device.

As will be explained in further detail with respect to various examples, the wearable device(s) 10 interact with the vehicle control system 40 in any number of different ways. For example, the wearable device(s) 10 may provide sensor data, identity information, stored information, streamed information, or other types of information to the vehicle. Based on this information, the vehicle may take any number of actions which may include one or more actions taken by the vehicle control system (or subsystems thereof). In addition, the vehicle 2 may communicate sensor data, identity information, stored information, streamed information or other types of information to the wearable device(s) 10.

Figure 2:
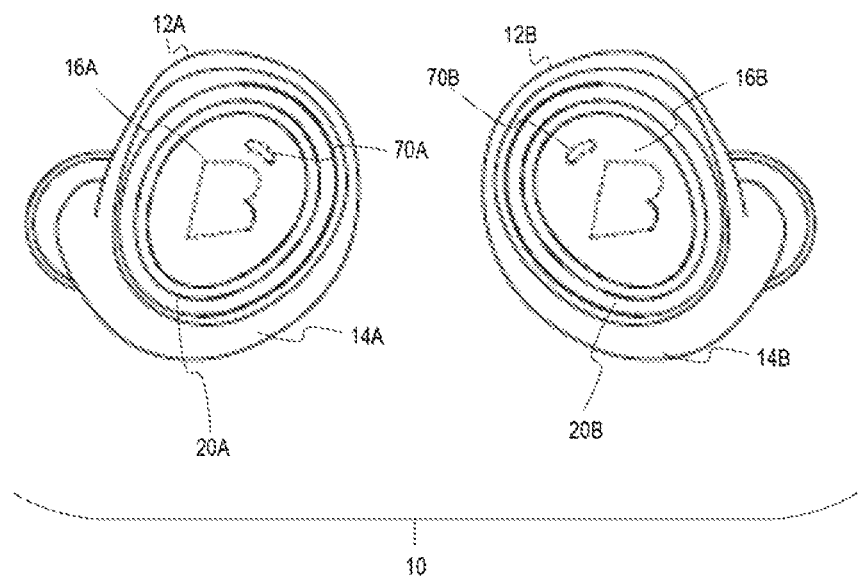
FIG. 2 illustrates a wearable device in the form of a set of ear pieces.

FIG. 2 illustrates one example of a wearable device in the form of a set of ear pieces 10 in greater detail. FIG. 1 illustrates a set of earpiece wearables 10 which includes a left earpiece 12A and a right earpiece 12B. Each of the earpieces wearables 12A, 12B has an earpiece wearable housing 14A, 14B which may be in the form of a protective shell or casing and may be an in-the-ear earpiece housing. A left infrared through ultraviolet spectrometer 16A and right infrared through ultraviolet spectrometer 16B are also shown. Each earpiece 12A, 12B may include one or more microphones 70A, 70B. Note that the air microphones 70A, 70B are outward facing such that the air microphones 70A, 70B may capture ambient environmental sound. It is to be understood that any number of microphones may be present including air conduction microphones, bone conduction microphones, or other audio sensors. There may be a corona 20A, 20B for each ear piece 12A, 12B which provides for lighting such as providing a light tube or light guide.

Figure 3:
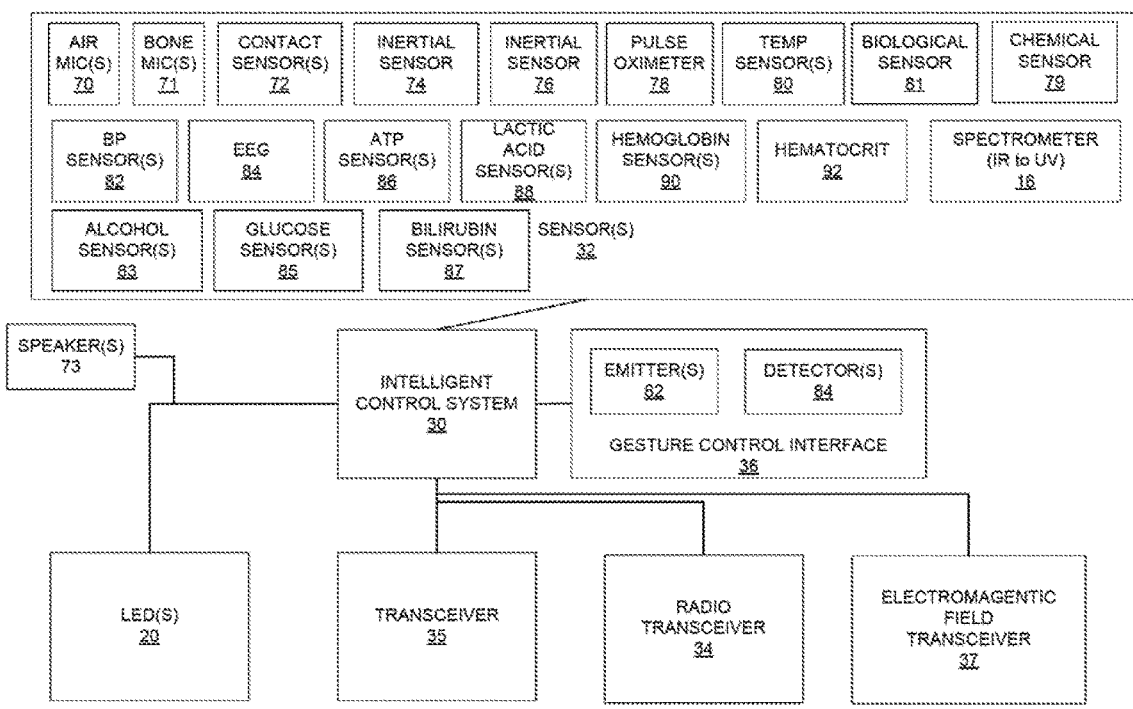
FIG. 3 is a block diagram illustrating a device.

FIG. 3 is a block diagram illustrating a device. The device may include one or more LEDs 20 electrically connected to an intelligent control system 30. The intelligent control system 30 may include one or more processors, digital signal processors, audio processors, microcontrollers, application specific integrated circuits, or other types of integrated circuits. The intelligent control system 30 may also be electrically connected to one or more sensors 32. Where the device is an earpiece, the sensor(s) may include inertial sensors 74, 76. Each inertial sensor 74, 76 may include an accelerometer, a gyro sensor or gyrometer, a magnetometer, a digital compass, or other type of inertial sensor. The sensor(s) 32 may also include one or more contact sensors 72 used to determine contact between a user and the earpiece, one or more bone conduction microphones 71, one or more air conduction microphones 70, one or more chemical sensors 79, a pulse oximeter 76, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device. These may include a blood pressure sensor 82, an electroencephalogram (EEG) 84, an Adenosine Triphosphate (ATP) sensor, a lactic acid sensor 88, a hemoglobin sensor 90, a hematocrit sensor 92 or other biological or chemical sensor.

A spectrometer 16 is also shown. The spectrometer 16 may be an infrared (IR) through ultraviolet (UV) spectrometer although it is contemplated that any number of wavelengths in the infrared, visible, or ultraviolet spectrums may be detected. The spectrometer 16 is preferably adapted to measure environmental wavelengths for analysis and recommendations and thus preferably is located on or at the external facing side of the device.

A gesture control interface 36 is also operatively connected to or integrated into the intelligent control system 30. The gesture control interface 36 may include one or more emitters 82 and one or more detectors 84 for sensing user gestures. The emitters may be of any number of types including infrared LEDs. The device may include a transceiver 35 which may allow for induction transmissions such as through near field magnetic induction. A short range transceiver 34 using Bluetooth, BLE, UWB, or other means of radio communication may also be present. The short range transceiver 34 may be used to communicate with the vehicle control system. In operation, the intelligent control system 30 may be configured to convey different information using one or more of the LED(s) 20 based on context or mode of operation of the device. The various sensors 32, the intelligent control system 30, and other electronic components may be located on the printed circuit board of the device. One or more speakers 73 may also be operatively connected to the intelligent control system 30.

An electromagnetic (E/M) field transceiver 37 or other type of receiver is also operatively connected to the intelligent control system 30 to link the intelligent control system 30 to the electromagnetic field of the user. The use of the E/M transceiver 37 allows the device to link electromagnetically into a personal area network or body area network or other device.

Figure 4:
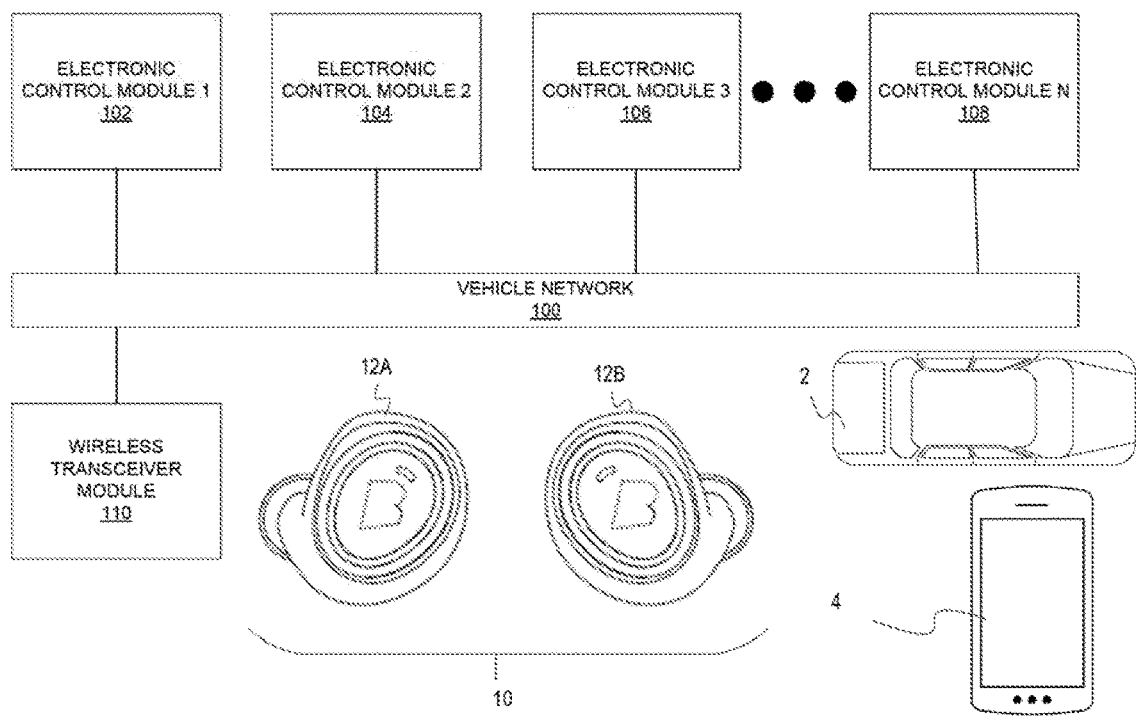
FIG. 4 illustrates a system which includes ear pieces in communication with a vehicle.

FIG. 4 illustrates another example of one or more wearable ear pieces 12A, 12B in operative communication with a vehicle. In FIG. 4, a vehicle network 100 is shown. According to one aspect, the wearable devices 12A, 12B may communicate information through a vehicle network 100 associated with a vehicle 2. Data, instructions, input, commands, files, or audio streams may be communicated over the vehicle network 100 or vehicle bus to and from the wearable devices 12A, 12B. Protocols which are used may include a Controller Area Network (CAN), Local Interconnect Network (LIN), or others including proprietary network protocols or network protocol overlays.

Various types of electronic control modules 102, 104, 106, 108 or electronic control units may communicate over the network 100 of the vehicle. These may include electronic modules such as an engine control unit (ECU), a transmission control unit (TCU), an anti-lock braking system (ABS), a body control module (BCM), a door control unit (DCU), an electric power steering control unit (PSCU), a human-machine interface (HMI), powertrain control module (PCM), speed control unit (SCU), telematic control unit (TCU), brake control unit (BCM), battery management system, entertainment system and numerous others. Any number of electronic control modules may be operatively connected to the vehicle network 100.

In one embodiment a wireless transceiver module 110 is operatively connected to a vehicle network 100 and it is the wireless transceiver module 110 which is in operative communication with one or more wearable devices such as wearable ear piece 12A, 12B.

Figure 5:
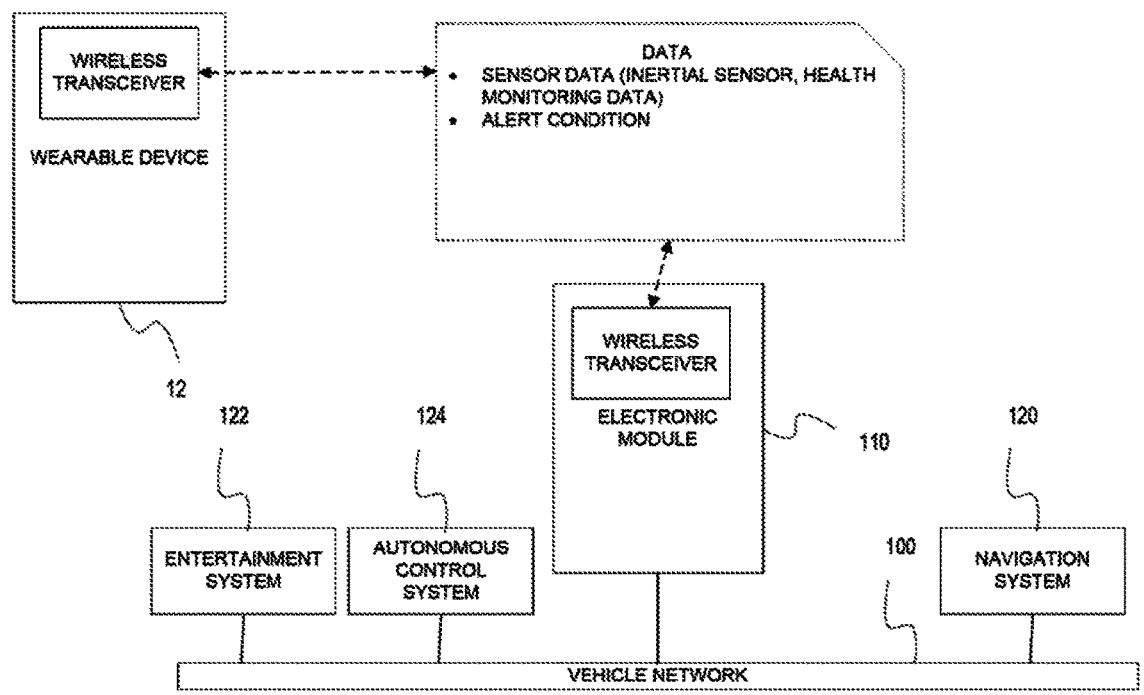
FIG. 5 illustrates a wearable device in communication with an entertainment system, navigation system and other systems having displays.

As shown in FIG. 5, one or more wearable devices 12 (including one or more ear pieces from one or more different vehicle occupants) may communicate with a navigation system 120 of a vehicle, an entertainment system 122, or an autonomous control system 124. Although the communication may be performed directly between the navigation system 120, entertainment system 122, or autonomous control system 124 and the and one or more ear pieces 12, in one embodiment a wireless transceiver module 110 may be operatively connected to the wearable ear piece 12 after the transceiver module 110 connects with or forms a wireless linkage with one or more of the wearable ear pieces 12. The wireless transceiver module 110 may use any number of different types of communications and protocols including Bluetooth, Bluetooth Low Energy (BLE), ultra-wideband, Wi-Fi, or otherwise.

According to another aspect, one or more wearable devices may provide for health monitoring of an individual such as a driver or passenger of the vehicle. The wearable devices may have any number of different sensors which may be used for monitoring the health of an individual or other physical parameters of an individual. Examples of sensors may include one or more inertial sensors such as an accelerometer, a gyro sensor or gyrometer, a magnetometer or other type of inertial sensor. As shown in FIG. 3, the sensor(s) 32 may also include one or more contact sensors 72, one or more bone conduction microphones 71, one or more air conduction microphones 70, one or more chemical sensors 79, a pulse oximeter 78, a temperature sensor 80, or other physiological or biological sensor(s). Further examples of physiological or biological sensors include an alcohol sensor 83, glucose sensor 85, or bilirubin sensor 87. Other examples of physiological or biological sensors may also be included in the device. These may include a blood pressure sensor 82, an electroencephalogram (EEG) 84, an Adenosine Triphosphate (ATP) sensor, a lactic acid sensor 88, a hemoglobin sensor 90, a hematocrit sensor 92 or other biological or chemical sensor. Data associated with the health monitoring may be displayed on one or more vehicle displays of the vehicle.

Figure 6:
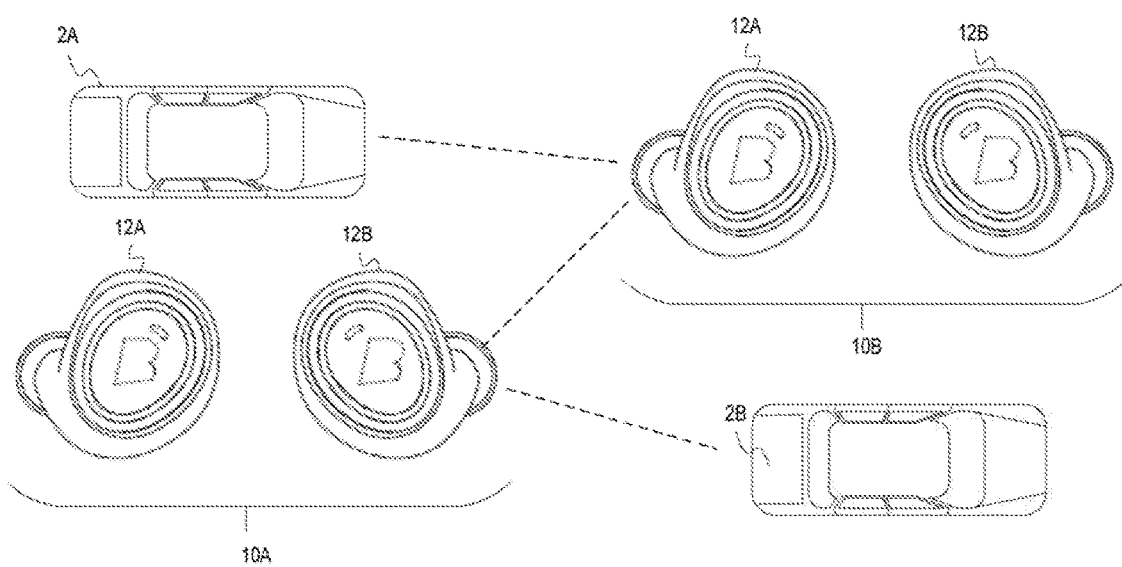
FIG. 6 illustrates a pair of ear piece wearable devices associated with an occupant of a first vehicle in operative communication with a pair of ear piece wearable devices associated with an occupant of a second vehicle.

FIG. 6 illustrates a first vehicle 2A and a second vehicle 2B. There is a set of ear pieces 10A associated with the first vehicle 2A such as may be worn by a driver of the first vehicle 2A or other occupant of the first vehicle 2A. There is a set of ear pieces 10B associated with the second vehicle 2B such as may be worn by a driver of the second vehicle 2B or other occupant of the second vehicle 2B. There are several different communication scenarios shown in FIG. 6.

In one example, the vehicle 2A is in operative communication with earpieces 10B worn by a driver of the vehicle 2B. In this example, inertial sensors in the ear pieces 10B may detect a sudden change in movement such as that associated with hard braking. In this instance an alert may be communicated to the vehicle 2A to warn the vehicle 2A that the vehicle in front of vehicle 2A, namely vehicle 2B is braking. The vehicle 2A may then perform any number of different actions or vehicle operations in response to this alert. The actions taken by vehicle 2A may depend upon whether vehicle 2A is a self-driving/autonomous vehicle in a self-driving mode or whether vehicle 2A is being operated by a driver. If vehicle 2A is being operated by a driver, vehicle 2A may alert the driver of a possible dangerous condition through making a warning sound, providing a visual indicator, or otherwise alerting the driver. If vehicle 2A is operating autonomously, or semi-autonomously, the vehicle may brake, change lanes, perform an analysis based on this data in addition to any other information the vehicle has acquired, or perform other vehicle operations. Alternatively, even if the vehicle is being operated by a driver, the vehicle may brake, change lanes, perform an analysis, or other vehicle operations.

In another example, the ear pieces 10A are in operative communication with the ear pieces 10B. In this example, an alert may be communicated from ear pieces 10B to ear pieces 10A for the benefit of the driver of vehicle 2A which is wearing the ear pieces 10 OA. This may be an audio alert or other type of alert to warn the driver of vehicle 2A of sudden movement associated with vehicle 2B.

Thus alert conditions may occur based on sensed data from one or more inertial sensors. Alert conditions may also occur based on driver or occupant health. Thus, for example if one or more of the physiological sensors detect an issue with a driver of a vehicle, an alert may be communicated to the second vehicle or to earpieces worn by a driver of the second vehicle. Thus, vehicle safety may be improved by providing advanced warning or supplemental warning of sudden changes in one vehicle to a second vehicle or a driver of the second vehicle.

The vehicle 2A may be configured to receive sensor data from the at least one wireless earpiece 10A within the vehicle 2A and/or the at least one wireless earpiece 10B within the separate and independent vehicle 2B and perform a vehicle operation based on the sensor data from the at least one wireless earpiece 10A within the vehicle and/or the at least one wireless earpiece within the separate and independent vehicle 10B. The sensor data from the at least one wireless earpiece 10B within the separate and independent vehicle 2B may be communicated between the vehicle network of the vehicle 2A and a vehicle network of the separate and independent vehicle 2B. The sensor data from the at least one wireless earpiece 10B within the separate and independent vehicle 2B may be communicated to the at least one wireless earpiece 10A within the vehicle 2A and from the at least one wireless earpiece 10A within the vehicle 2A to the vehicle network of the vehicle 2A.

Various methods, system, and apparatus have been shown and described relating to vehicles with wearable integration or communication. The present invention is not to be limited to these specific examples but contemplates any number of related methods, system, and apparatus and these examples may vary based on the specific type of vehicle, the specific type of wearable device, and other considerations.

What is claimed is:

1. A system comprising:
    a vehicle;
    a vehicle network disposed within the vehicle;
    a set of wireless earpieces comprising a left wireless earpiece and a right wireless earpiece for use by an individual within the vehicle, each of the left wireless earpiece and the right wireless earpiece comprising an earpiece housing, an intelligent control system disposed within the earpiece housing, a speaker operatively connected to the intelligent control system, a microphone operatively connected to the intelligent control system and an inertial sensor operatively connected to the intelligent control system and wherein at least one of the left wireless earpiece and the right wireless earpiece further comprises a health monitoring sensor operatively connected to the intelligent control system;
    wherein the vehicle is configured to receive sensor data from the set of wireless earpieces within the vehicle, the sensor data comprising inertial sensor data from the inertial sensors of the set of wireless earpieces and health monitoring data from the health monitoring sensor of the at least one wireless earpiece;
    wherein the vehicle is configured to receive sensor data from a second set of wireless earpieces within a separate and independent vehicle;
    wherein the vehicle is configured to perform a vehicle operation based on the sensor data from the set of wireless earpieces within the vehicle or the second set of wireless earpieces within the separate and independent vehicle.

2. The system of claim 1 wherein the sensor data from the second set of wireless earpieces within the separate and independent vehicle is communicated between the vehicle network of the vehicle and a vehicle network of the separate and independent vehicle.

3. The system of claim 1 wherein the sensor data from the second set of wireless earpieces within the separate and independent vehicle is communicated to the set of wireless earpieces within the vehicle and from the set of wireless earpieces within the vehicle to the vehicle network of the vehicle.

4. The system of claim 1 wherein the set of wireless earpieces for use by the individual within the vehicle is configured to determine a warning condition based on sensed data from the inertial sensor.

5. The system of claim 1 wherein the vehicle network is configured to electronically send a warning message to the second set of wireless earpieces within the separate and independent vehicle.

6. The system of claim 1 wherein the vehicle network is configured to electronically receive a warning message from the second set of wireless earpieces within the separate and independent vehicle.

7. The system of claim 1 wherein the set of wireless earpieces for use by the individual within the vehicle is configured to determine a warning condition based the health monitoring data.

8. A method comprising:
    providing a set of wireless earpieces comprising a left wireless earpiece and a right wireless earpiece wherein each of the left wireless earpiece and the right wireless earpiece comprising an earpiece housing, an intelligent control system disposed within the earpiece housing, a speaker operatively connected to the intelligent control system, a microphone operatively connected to the intelligent control system and an inertial sensor operatively connected to the intelligent control system and wherein at least one of the left wireless earpiece and the right wireless earpiece further comprises a health monitoring sensor operatively connected to the intelligent control system;
    sensing inertial data with the inertial sensor of the left wireless earpiece and the inertial sensor of the right wireless earpiece of the set of wireless earpieces within a first vehicle;
    sensing health data with a health monitoring sensor of the set of wireless earpieces within the first vehicle
    determining by the set of wireless earpieces within the first vehicle an alert condition based on at least one of the inertial data and the health data; and
    wirelessly communicating a message from the set of wireless earpieces within a first vehicle to a wireless ear piece within a second vehicle, the message indicating occurrence of the alert condition.

9. A method comprising:
    providing a set of wireless earpieces comprising a left wireless earpiece and a right wireless earpiece wherein each of the left wireless earpiece and the right wireless earpiece comprising an earpiece housing, an intelligent control system disposed within the earpiece housing, a speaker operatively connected to the intelligent control system, a microphone operatively connected to the intelligent control system and an inertial sensor operatively connected to the intelligent control system and wherein at least one of the left wireless earpiece and the right wireless earpiece further comprises a health monitoring sensor operatively connected to the intelligent control system;
sensing inertial data with an inertial sensor of at least one of the left wireless or the right wireless earpiece within a first vehicle;
sensing physiological data with a physiological sensor of at least one of the left wireless earpiece or the right wireless earpiece within the first vehicle;
determining by at least one of the left wireless earpiece and the right wireless earpiece within the first vehicle an alert condition based on sensed data comprising the inertial data and the physiological data; and
wirelessly communicating a message from the wireless earpiece within the first vehicle to a second vehicle, the message indicating occurrence of the alert condition.

* * * * *